United States Patent
Teeslink et al.

(10) Patent No.: US 8,353,929 B2
(45) Date of Patent: Jan. 15, 2013

(54) VASCULAR WOUND CLOSING APPARATUS AND METHOD

(75) Inventors: Charles Rex Teeslink, Augusta, GA (US); Griscom Bettle, Sarasota, FL (US)

(73) Assignee: Wound Care 360, LLC, Boca Grande, FL (US)

( * ) Notice: Subject to any disclaimer, the term of this patent is extended or adjusted under 35 U.S.C. 154(b) by 0 days.

(21) Appl. No.: 13/551,699

(22) Filed: Jul. 18, 2012

(65) Prior Publication Data

US 2012/0277792 A1 Nov. 1, 2012

Related U.S. Application Data

(60) Division of application No. 13/421,253, filed on Mar. 15, 2012, now Pat. No. 8,277,483, which is a continuation of application No. 13/105,255, filed on May 11, 2011, now abandoned.

(60) Provisional application No. 61/461,923, filed on Jan. 25, 2011, provisional application No. 61/463,373, filed on Feb. 16, 2011.

(51) Int. Cl.
*A61B 17/08* (2006.01)

(52) U.S. Cl. ......... 606/215; 606/201; 606/203; 606/213

(58) Field of Classification Search ............... 606/151, 606/157, 158, 201, 213, 215, 602, 603; 602/53
See application file for complete search history.

(56) References Cited

U.S. PATENT DOCUMENTS

| | | |
|---|---|---|
| 4,773,421 A | 9/1988 | Davis |
| 5,127,412 A | 7/1992 | Cosmetto et al. |
| 5,263,965 A | 11/1993 | Roth |
| 5,307,811 A | 5/1994 | Sigwart et al. |
| 5,342,388 A | 8/1994 | Toller |
| 5,690,610 A * | 11/1997 | Ito et al. .................... 602/53 |
| 5,690,674 A | 11/1997 | Diaz |
| 5,728,120 A | 3/1998 | Shani et al. |
| 5,746,755 A | 5/1998 | Wood et al. |

(Continued)

FOREIGN PATENT DOCUMENTS

WO WO 2010/118312 10/2010

OTHER PUBLICATIONS

Chen et al. *Vascular Closure Device-related Complications After Percutaneous Coronary Intervention*. J Taiwan Cardiovasc Interv 1 (2010):24-27.

(Continued)

*Primary Examiner* — Corrine M McDermott
*Assistant Examiner* — Alexander Orkin
(74) *Attorney, Agent, or Firm* — Hovey Williams LLP

(57) ABSTRACT

Wound closure apparatus is provided including a body having an elongated, lowermost force-transmitting surface operable to be placed in a proximal, external, wound-closing position on a patient, together with a force-exerting assembly coupled with the body and operable to exert a downwardly directed force serving to generate wound-closing pressure against the patient's tissue. The force-transmitting surface is preferably three-dimensionally asymmetric so that forces of different magnitude are exerted at different locations along the length of the surface. The apparatus is especially designed for the closure of wounds attendant to endovascular interventions, e.g., a femoral artery puncture wound incident to percutaneous cardiac intervention (PCI), and is capable of quickly effecting wound closure with a time-to-ambulation (TTA) of approximately 60 minutes, and with a very low complication rate.

10 Claims, 4 Drawing Sheets

U.S. PATENT DOCUMENTS

| | | |
|---|---|---|
| 5,792,173 A | 8/1998 | Breen et al. |
| 5,919,207 A | 7/1999 | Taheri |
| 5,964,782 A | 10/1999 | Lafontaine et al. |
| 6,074,356 A | 6/2000 | Starkey et al. |
| 6,187,347 B1 | 2/2001 | Patterson et al. |
| 6,264,673 B1 | 7/2001 | Egnelöv et al. |
| 6,331,182 B1 | 12/2001 | Tiefenbrun et al. |
| 6,471,715 B1 | 10/2002 | Weiss |
| 6,752,810 B1 | 6/2004 | Gao et al. |
| 7,081,124 B2 | 7/2006 | Sancoff et al. |
| 7,087,060 B2 | 8/2006 | Clark |
| 7,175,646 B2 | 2/2007 | Brenneman et al. |
| 7,637,921 B2 | 12/2009 | Åkerfeldt et al. |
| 7,780,612 B2 | 8/2010 | Ross |
| 8,034,009 B2 | 10/2011 | Bates et al. |
| 2003/0028214 A1 | 2/2003 | Benz et al. |
| 2003/0163160 A1 | 8/2003 | O'Malley et al. |
| 2004/0098034 A1 | 5/2004 | O'Connor |
| 2004/0143289 A1 | 7/2004 | Zahler et al. |
| 2004/0162577 A1 | 8/2004 | Tarone |
| 2006/0089667 A1 | 4/2006 | Ben-David |
| 2006/0229662 A1 | 10/2006 | Finkielsztein et al. |
| 2006/0229663 A1 | 10/2006 | Chiu et al. |
| 2009/0082790 A1 | 3/2009 | Shad et al. |
| 2009/0281569 A1 | 11/2009 | Alghamdi |
| 2011/0152889 A1 | 6/2011 | Ashland |
| 2011/0196417 A1 | 8/2011 | Clark |
| 2011/0202089 A1 | 8/2011 | Sun |
| 2011/0245868 A1 | 10/2011 | Teeslink et al. |

OTHER PUBLICATIONS

International Search Report and Written Opinion dated Jul. 25, 2012, in corresponding PCT Application No. PCT/US2012/022486 filed Jan. 25, 2012.

* cited by examiner

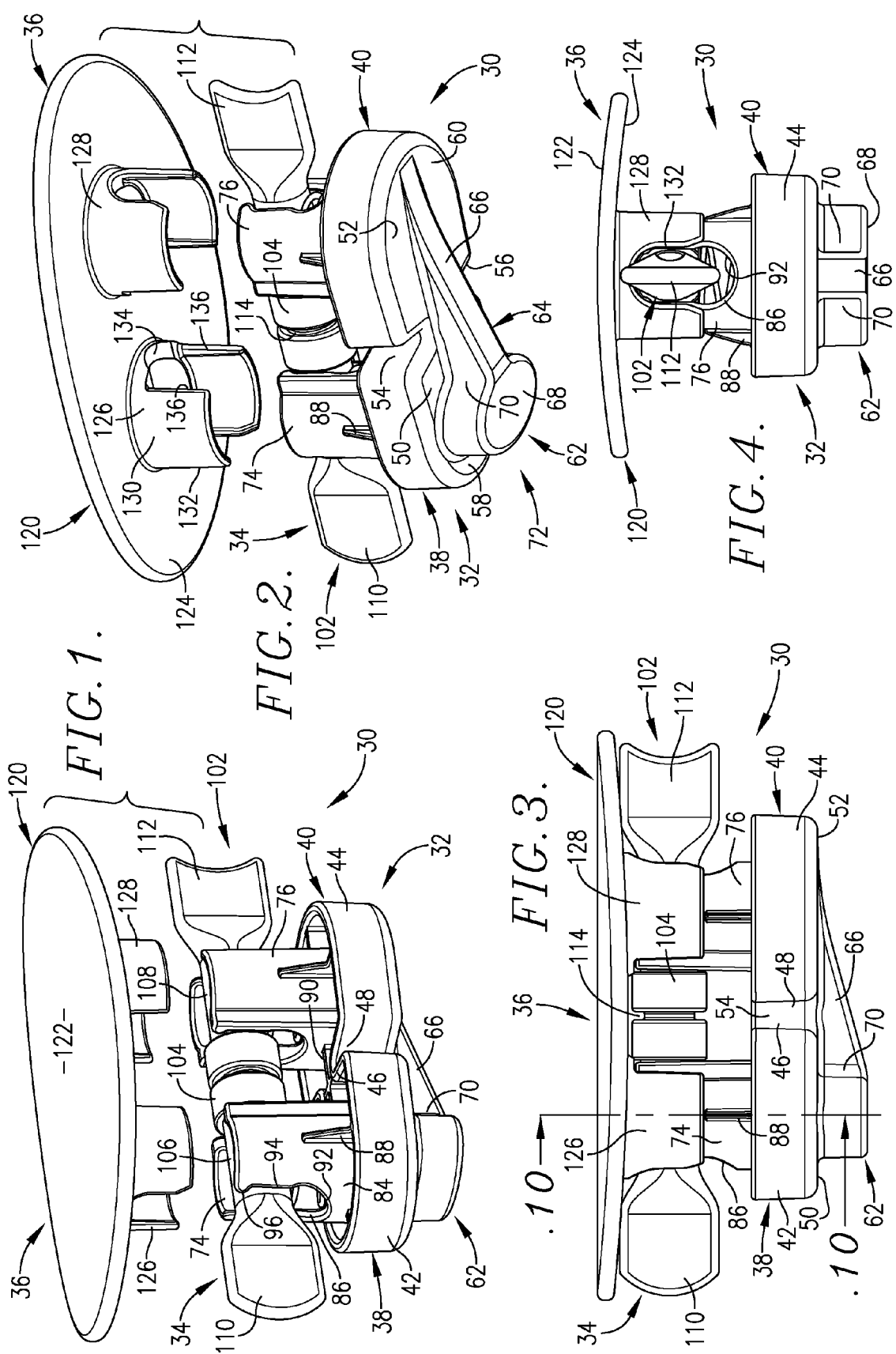

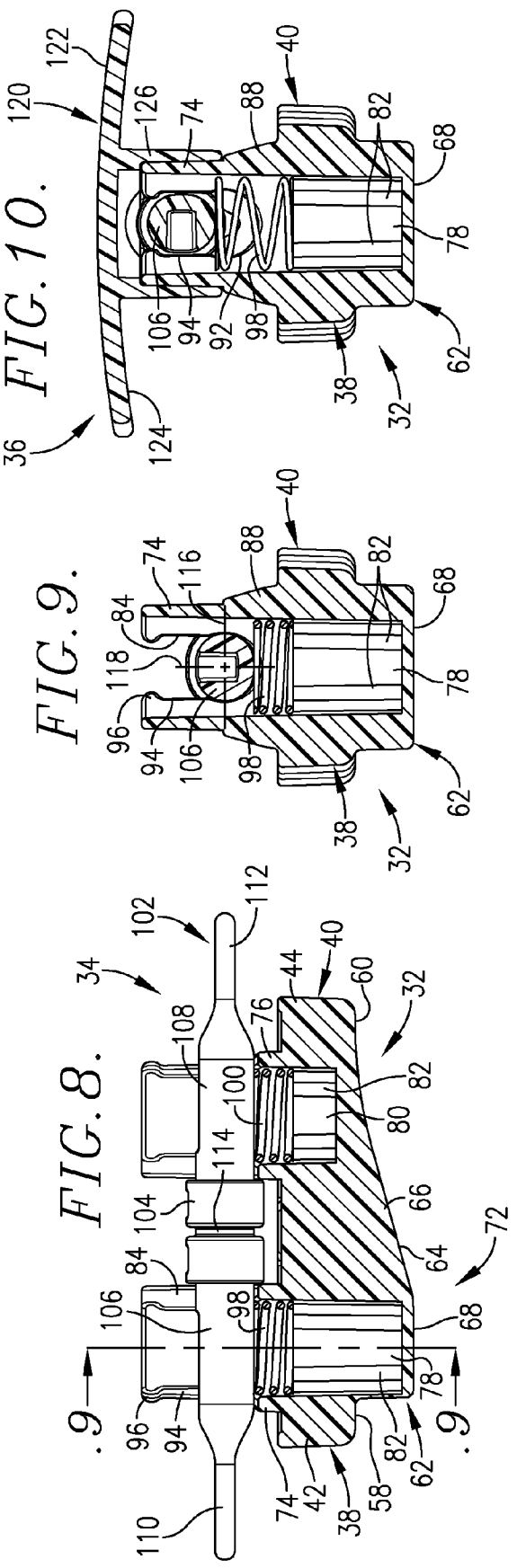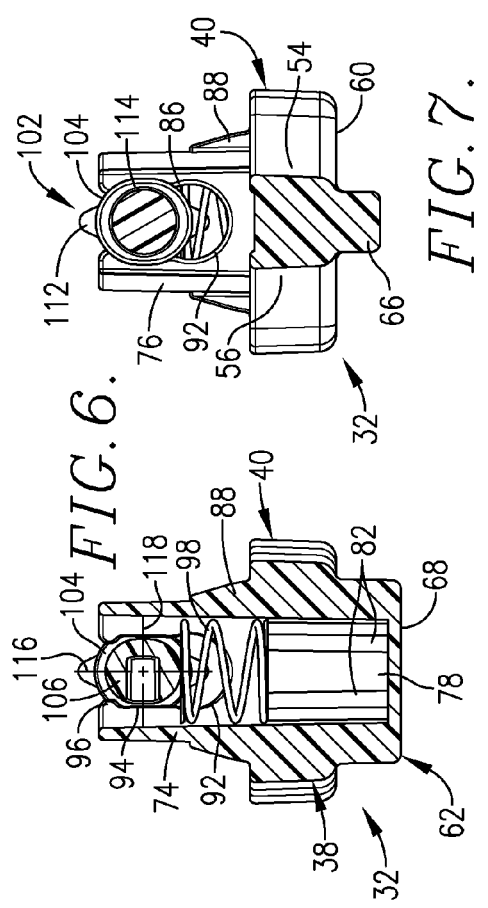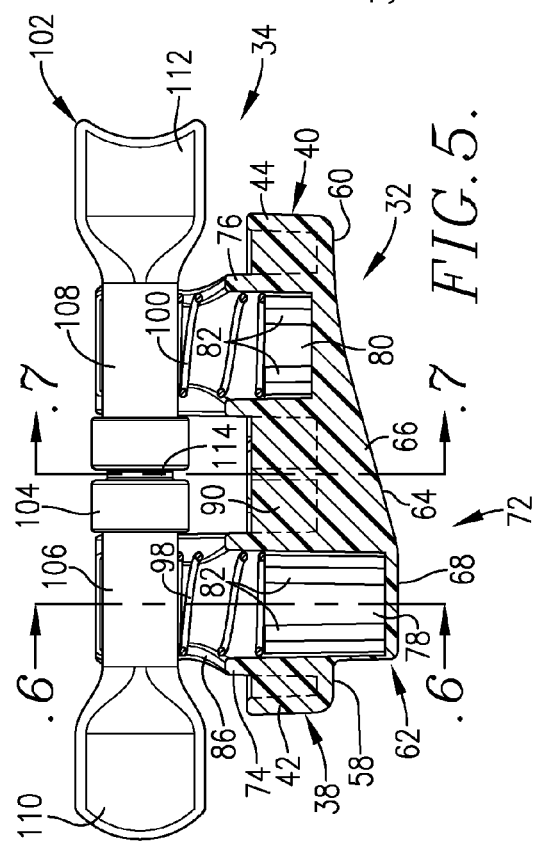

VASCULAR WOUND CLOSING APPARATUS AND METHOD

CROSS-REFERENCE TO RELATED APPLICATION

This application is a division of identically-titled application Ser. No. 13/421,253 filed Mar. 15, 2012, now U.S. Pat. No. 8,277,483, which is a continuation of identically-titled application Ser. No. 13/105,255 filed May 11, 2011, now abandoned, and also claims the benefit of Provisional Application Ser. No. 61/461,923, filed Jan. 25, 2011, and Provisional Application Ser. No. 61/463,373, filed Feb. 16, 2011, all of which are incorporated by reference herein in their entirety.

BACKGROUND OF THE INVENTION

1. Field of the Invention

The present invention is broadly concerned with improved apparatus and methods for closure of wounds in the tissue of patients, and especially wounds attendant to endovascular interventions, such as percutaneous cardiac intervention (PCI,) wherein closure is defined as the time from removal of the catheter to ambulating the patient. More particularly, the invention is concerned with such apparatus and methods which employs a rigid wound-closing body adapted to be placed adjacent and along the length of the wound, together with a force-exerting assembly operable to create forces which generate relatively high pressures on the patient's skin and tissue adjacent the wound. In preferred forms, the rigid body has a three-dimensionally asymmetric lower force-transmitting surface so as to exert forces of different magnitudes at different locations along the force-transmitting surface. Also, the force-transmitting surface is preferably exerted substantially constantly and in a substantially time-invariant manner.

2. Description of the Prior Art

Endovascular interventions such as PCI are widely accepted as a practical treatment option for coronary artery disease. For example, femoral artery puncture is commonly used in endovascular diagnostic and interventional procedures. Alternately, access may be made via the right radial or brachial artery. Such procedures are now commonly performed on an out-patient basis. In the case of a femoral arterial intervention, a puncture wound is made with a cannula to create an oblique subcutaneous tract and a terminal arteriotomy, followed by placement of a sheath within the tract. A catheter is then threaded through the sheath and into the adjacent artery, so that access can be had to the coronary arteries. After the diagnosis or intervention is completed, the catheter is withdrawn, the sheath is removed, and steps must be taken to close the wound. Wound closure typically involves compression to control bleeding until hemostasis occurs. Ideally, wound closure serves to minimize blood loss, effect hemostasis, and render the patient ambulatory in a relatively short period of time.

Poorly executed wound closures may give rise to complications which are costly, increase hospital stays and affect morbidity. For example, inadequate hemostasis can lead to significant blood loss, patient discomfort, vessel occlusion, thrombosis, formation of arteriovenous fistula, and pseudoaneurysm requiring surgical intervention and/or steps to avoid infections. Complications at the access site due to arterial cannulation occur in 1%-5% of cases, but may be as high as 14% with some interventional procedures.

Traditionally, wound closure has been a manual operation where a physician or nurse used manual hand pressure, using either one or two hands. One-handed manual pressure is usually carried out over a period of 30 minutes with a time to ambulation (TTA) of 4-6 hours. Two-handed manual pressure (often referred to as the "gold standard" of wound closure) ideally achieves optimal wound closure. In this technique, the healthcare professional's left hand exerts a semi-occlusive pressure upstream (closer to the heart) of the arteriotomy to moderate blood pressure fluctuations and to reduce the mean blood pressure from the heart without denying blood flow downstream. The professional's right hand holds an occlusive pressure over the arteriotomy, tract, and insertion site. This is continued for a period of approximately 30 minutes. However, in actual practice, there are a number of significant problems. For example, manual pressure that is too firm does not allow sufficient clotting factors to accumulate at the arteriotomy. Moreover, manual pressure along the tract varies because the tips of the four fingers of the right hand are not flat. Even more important, the person exerting manual pressure can tire during the 30-minute holding time, or the fingers may move or may not be placed properly. The person may also temporarily stop the application of pressure to examine the wound, causing a disruption of the maturing clot. Finally, different body types present different manual pressure issues, e.g., if the panniculus intrudes on the person's left hand, pressure variations may be induced as the patient breathes and the panniculus moves. TTA for this two-handed procedure is again normally 4-6 hours.

Manual techniques can be supplemented with use of applied hemostasis adjuncts, which reduce the time to hemostasis (TTH) to 5-6 minutes, but do not lower TTA because there is no force on the arteriotomy after hemostasis is achieved. Manual pressure may also be supplemented with external devices, such as C-clamps or sand bags. These combined techniques have many of the same problems as straightforward manual pressure closures, and the external devices may be difficult to deploy on obese patients. Thus, while manual procedures are of long standing, they are deficient in that they can be tiring, require careful training, and represent inefficient use of the time of valuable medical personnel.

Other closure techniques involve use of an intra-arterial anchor giving a TTH of about five minutes and a TTA of about 2-3 hours. Drawbacks of these procedures include a maximum French size of 8 Fr and the fact that the anchor and collagen plug must be left in the body for up to 90 days. Suture-mediated intra-arterial anchor techniques have also been used, but these are deficient in that the sutures remain in the body until absorbed, and nonetheless require that the anchor and plug be left in the body for an extended period. Finally, intra-tract closure has been used where the arteriotomy is mechanically stretched and then "boomerangs" back to an 18-gauge needle diameter. In these procedures, a heparin-neutralizing drug is deployed within the wound tract, and manual pressure is still required to close the 18-gauge needle hole.

In recent years, new, larger interventional devices of up to 20 Fr are being used to perform tasks like operations within the heart itself. No existing closure device is indicated for these large interventions, and resort must be had to manual pressure or surgical techniques to close the large wounds.

In response to these problems, various specialized vascular closure devices (VCDs) have been proposed, such as the device disclosed in U.S. Pat. No. 5,307,811 and commercialized under the designation "FemoStop." While these and other VCDs have achieved widespread use, no prior VCD has fully solved the problems inherent in wound closures. Dauerman et al. (*J AM COLL CARDIOLL.* 2007; 50 (17) Elsevier Science)—"Vascular Closure Devices: The Second Decade" described an ideal VCD:

The patient factors influencing closure success notwithstanding the "ideal" closure device remains to be developed. What would this device look like? 1) A single device capable of providing successful closure for all patient and success site anatomical variations; 2) an atraumatic device without a foreign body or vascular alteration of the femoral artery; and 3) a simple-to-use device with >95% procedural success and low cost.

The prior art uses the terms "pressure" and "force" loosely. A person exerting force through small fingers would apply more pressure than a person exerting the same force with larger fingers. A further complication is that the heart is beating, making the pressure (sum of internal and external pressure) variable. What is critical is controlling blood flow. If there were no flow restriction, the arteriotomy would leak, resulting in a hematoma. If there were complete flow restriction, then the downstream extremities would be starved of oxygen and the arteriotomy would be starved of necessary clotting factors. Hence, the ideal VCD is one in which flow is restricted, but not excessively.

Accordingly, there is an unfulfilled need in the art for a simple-to-use VCD which closely mimics "gold standard" manual wound closure, has a complication rate of <1%, can be used on all types of patients, gives very low TTH and TTA values, and does not involve residual drugs, sutures, or anchoring devices.

SUMMARY OF THE INVENTION

The present invention overcomes the problems outlined above and provides VCDs and corresponding methods which have many outstanding features. For example, preferred embodiments of the invention used in the context of arterial PCI procedures are characterized by:

- a TTA on the order of 60 minutes for diagnostic PCI procedures;
- a complication rate of <1%;
- atraumatic, essentially painless wound closure with no residual foreign materials in the wound or vascular alterations;
- targeted asymmetric tissue pressures, with a larger non-occlusive pressure applied upstream of the arteriotomy to lower the patient's blood flow, with decreasing pressures downstream of the arteriotomy;
- substantially time-invariant wound closure pressures on the tissue;
- skin inversion adjacent the wound by means of a Z-stitch suture together with a rigid, force-transmitting surface including a transverse section positioned above the arteriotomy and generating force of greater than about 20 lbs., but not greater than the suture-rupturing force, and an obliquely oriented, axially extending section, which generates decreasing pressures downstream of the arteriotomy;
- secondary wound closure force through use of an adhesive sheet stretched over the device and adhered to the patient's skin on either side of the site;
- virtually no blood loss during wound closure;
- different sheath sizes, blood chemistries (e.g., INR>1.5, or the presence of blood thinners), and degrees of intervention can be accommodated by increasing the closure time;
- a device cost on the order of $100;
- wound closure procedure is typically learned with less than ten diagnostic procedures.

In the ensuing description, the methods and apparatus of the invention are described with particular reference to wounds incident to an arterial intervention procedure. However, it should be understood that the invention is equally applicable to other types of vascular vessel procedures where a wound includes an opening in a non-arterial vascular vessel, such as a venous vessel.

In one aspect of the invention, apparatus is provided to close a wound in a patient's tissue where the wound presents an insertion site and an elongated, obliquely oriented tract extending into the patient's tissue and in communication with the insertion site. Such apparatus comprises a body having an elongated, rigid force-transmitting surface and operable to be placed in an external wound-closing position with the force-transmitting surface proximal to the patient's skin, adjacent the wound and in general axial alignment with the tract. A force-exerting assembly is coupled with the body and is operable to exert forces of different magnitudes at different locations along the length of the force-transmitting surface in order to close the wound. In preferred forms, the force-transmitting surface is three-dimensionally asymmetric, and comprises first and second, preferably coplanar, surface sections having different force-transmitting areas respectively. Also, a third force-transmitting surface is provided which bridges the first and second surface sections and is generally T-shaped in configuration, presenting an elongated segment and a segment transverse to the elongated segment. Desirably, the elongated segment is obliquely oriented relative to the first and second surface sections. The force-exerting assembly is operable to exert a force which generates a force on the tissue of at least about 10 lbs., and more preferably at least about 20 lbs.

The overall force-exerting assembly also includes structure for securing the body to the patient's tissue, and a mechanism including a shiftable component for generating a mechanically-derived force through the force-transmitting surface. Such securement structure preferably comprises a suture passing through the patient's tissue and tied to the body to hold the body in the wound-closing position. The suture may be in the form of a known Z-stitch suture which serves to invert the patient's skin at the wound site. The mechanism is preferably in the form of a biasing structure including at least one (and more preferably two) spring(s). Secondary forces may be generated by means of an adhesive sheet stretched over the device and adhered to the patient's skin on opposite sides of the wound site.

Advantageously, the force-exerting assembly is designed to exert a substantially constant and time-invariant force through the force-transmitting surface; this, coupled with the preferred asymmetric force application serves to reduce the patient's blood pressure and flow within the artery and especially at the arteriotomy.

BRIEF DESCRIPTION OF THE DRAWINGS

FIG. 1 is an exploded, upper perspective view of the preferred wound-closing apparatus of the invention;

FIG. 2 is an exploded, lower perspective view of the preferred wound-closing apparatus of the invention;

FIG. 3 is a side elevational view of the fully assembled apparatus;

FIG. 4 is an end view of the fully assembled apparatus;

FIG. 5 is a side view in partial vertical section illustrating the base portion of the apparatus, with the force-exerting springs in the released position thereof;

FIG. 6 is a vertical sectional view taken along the line 6-6 of FIG. 5;

FIG. 7 is a vertical sectional view taken along the line 7-7 of FIG. 5;

FIG. 8 is a side view in partial vertical section illustrating the base portion of the apparatus, with the force-exerting springs in the cocked position thereof;

FIG. 9 is a vertical section view taken along the 9-9 of FIG. 8;

FIG. 10 is a vertical section view taken along the line 10-10 of FIG. 3;

DETAILED DESCRIPTION OF THE PREFERRED EMBODIMENT

The Preferred Wound Closure Apparatus

Figure 11:
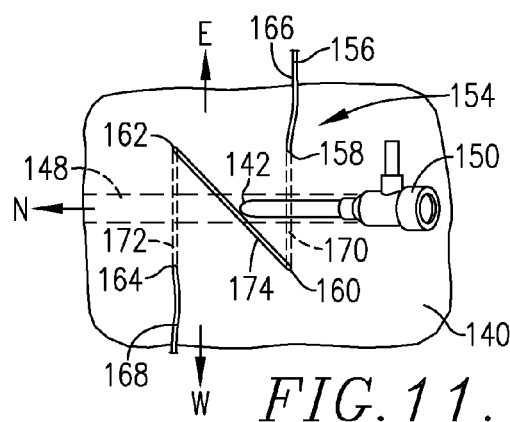
FIG. 11 is a top view illustrating a catheter sheath positioned within a wound attendant to a vascular procedure, and further illustrating the first step in the preferred method of the invention wherein a Z-shaped stitch has been created with a suture in the patient's tissue.

Turning now to the drawings, apparatus 30 operable to close a wound in a patient's tissue is illustrated in FIGS. 1-4. The apparatus 30 is particularly designed for closure of wounds attendant to an endovascular (i.e., arterial or venous) intervention involving, e.g., a femoral artery puncture where the wound presents an insertion site, an elongated, obliquely oriented tract extending into the patient's tissue and communicating with the insertion site and an arteriotomy. Broadly speaking, the apparatus 30 includes a force-transmitting body 32 having a force-exerting assembly 34 together with a removable cover or "hat" 36.

As used herein, terms such as "upper" and "lower," "top" and "bottom," and "downwardly" and "upwardly" and the like are used for convenience and because of the fact that the apparatus 30 is normally positioned in an upright orientation on a patient with the cover 36 being directly above the body 32. However, if the apparatus 30 were to be placed in a different orientation (e.g., sideways) the cover 36 would nonetheless be deemed to be above the body 32, and the above terms are intended to embrace all such different orientations.

In more detail, the body 32 is of rigid unitary construction and is formed of an appropriate synthetic resin material. The body 32 has first and second, axially aligned cup-like sections 38 and 40, each with an arcuate, upstanding sidewall 42, 44, a bifurcated, rectilinear end wall 46, 48, and a bottom wall 50, 52 serving to interconnect the section 38, 40. A pair of grooves 54 and 56 are provided between each of the end wall bifurcations as best seen in FIG. 2. The bottom walls 50, 52 are configured to present first and second substantially flat and coplanar force-transmitting sections 58 and 60; it will be observed that the area of section 58 is smaller than that of section 60, and this is important for purposes to be described.

A protruding, downwardly extending segment 62 bridges and is integral with the bottom walls 50, 52 and presents a lowermost, generally T-shaped third force-transmitting surface 64 which bridges the sections 38 and 40. The surface 64 presents an elongated, obliquely oriented and progressively tapered segment 66 extending from the end of bottom wall 52 to a point below bottom wall 50. Another surface segment 68 is generally transverse to the elongated segment 66 and is substantially centrally located below bottom wall 50. The segment 62 further includes a generally U-shaped sidewall 70 extending downwardly from the bottom walls 50, 52 of the sections 38, 40.

It will be appreciated that the body 32 presents an overall force-transmitting surface 72 made up of the force-transmitting sections 58, 60, 64, and 68. This surface 72 is three-dimensionally asymmetric owing to the fact that the area of first surface section 58 is less than that of the second surface section 60 (so that the overall surface 72 is asymmetric in a fore-and-aft direction), and because of the fact that the inclined surface segment 66 and transverse surface segment 68 are positioned below the first and second sections 58, 60 (so that the overall surface 72 is asymmetric in a vertical direction). Moreover, the inclined segment 66 provides an increasing and progressive force gradient from the second surface section 60 to the transverse segment 68.

The sections 38 and 40 are each equipped with an upstanding, slotted, tubular member 74 or 76 which extend upwardly from the upper surfaces of the corresponding bottom walls 50, 52. As best seen in FIGS. 5 and 8, an elongated, downwardly extending cylindrical opening 78 is formed in bottom wall 50 and protruding segment 62 directly beneath and coaxial with the tubular member 74. Likewise, a shorter, downwardly extending cylindrical opening 80 is provided directly beneath and coaxial with tubular member 76. Each of the openings 78, 80 has a plurality of elongated, upright, circumferentially spaced apart, inwardly extending, integral ribs 82.

The configuration of the tubular members 74, 76 is identical, and therefore only the construction of member 74 will be described in detail. Specifically, member 74 has an upstanding sidewall 84 with a pair of specially configured and opposed slots 86 formed therein. The sidewall 84 is reinforced by means of external gussets 88 and braces 90. Each slot 86 includes a lowermost, substantially frusto-circular portion 92, an intermediate upright portion 94, and an uppermost, inwardly extending lip portion 96.

The force-exerting assembly 34 generally includes a pair of identical, helically coiled springs 98, 100 respectively housed within a corresponding tubular member 74, 76 and supported therein by means of the adjacent upstanding ribs 82. The overall assembly 34 further includes an elongated, axially rotatable paddle-like operator 102, which extends fore and aft and is received by the opposed slots 86, so that the operator extends through and is supported by both of the tubular members 74, 76 and engages the springs 98, 100. The operator 102 is likewise formed of synthetic resin material and includes a central segment 104, a pair of identical, elongated, slotted, oval-shaped segments 106 and 108 on opposite sides of the central segment 104, and fore-and-aft segments 110, 112.

Referring to FIG. 5, it will be observed that the central segment 104 is cylindrical in configuration and has a central, peripheral, suture-receiving groove 114 formed therein. The oval segments 106, 108 are situated within the tubular members 74, 76 and have major axes 116 and transverse, minor axes 118 (FIG. 6). The fore end segment 110 has a rounded outer edge, whereas the corresponding aft end segment 112 has a recessed trailing edge. In this fashion, the operator 102 has an arrow-like shape along the length thereof.

The operator 102 serves to allow selective compression of the springs 98, 100 so as to maintain the springs in a cocked position as best seen in FIGS. 8 and 9. Upon 90° rotation of operator 102, the springs 98, 100 are released to a force-exerting position illustrated in FIGS. 5-7 and 10. In more detail, if it is desired to cock the springs 98, 100, the operator 102, in the FIG. 5-7 position where the major axes 116 are upright, is pressed downwardly through the upright portions 94 of the slots 86 until the bottom peripheries of the oval segments 106, 108 engage the bottoms of the frusto-circular portions 92. Thereupon, the operator 102 is rotated 90° in either direction so that the major axes 116 are substantially horizontal and the oval segments 106, 108 are captively retained by the frusto-circular portions 92. When it is desired to release the springs 98, 100, this operation is reversed, i.e., the operator 102 is rotated 90° until the major axes are again upright. The springs 98, 100 then urge the operator 102 upwardly to the FIGS. 5-7 position, with the lip portions 96 of the slots 86 serving to retain the operator 102 within the slots 86.

The cover 36 includes an uppermost wall 120 which is gently arcuate in cross-section and presents an upper surface 122 and a lower surface 124. A pair of depending, slotted tubular members 126, 128 extend from bottom surface 124 and are in alignment with the tubular members 74, 76. The members 126, 128 are identical, and therefore only member 126 will be described in detail. As best seen in FIGS. 1, 2, and 4, the member 126 includes a sidewall 130 with a pair of opposed slots 132. Each slot 132 includes an uppermost arcuate portion 134 and a substantially rectilinear portion 136. The tubular members 126, 128 are of slightly larger diameter than the corresponding tubular members 74, 76, allowing the cover 36 to be positioned over body 32 and pressed downwardly over the tubular members 74, 76 to assume the position depicted in FIGS. 3-4. It will be observed in this respect that the slots 86 of the tubular members 74, 76 are in substantial alignment with the slots 132 of the tubular members 126, 128.

Preferred Method of Use of the Wound Closure Apparatus

Figure 12:
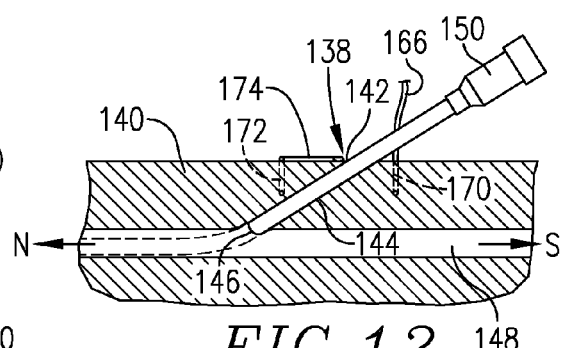
FIG. 12 is a sectional view of the wound, sheath, and suture depicted in FIG. 11.
Figure 13:
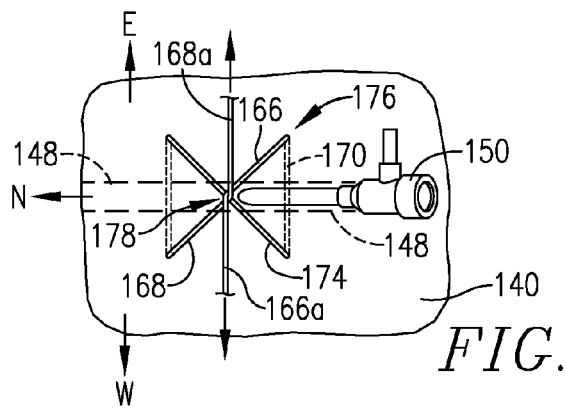
FIG. 13 is a top view illustrating the next step in the preferred method wherein the ends of the suture are tied to define an X-shaped stitch over the patient's skin.
Figure 14:
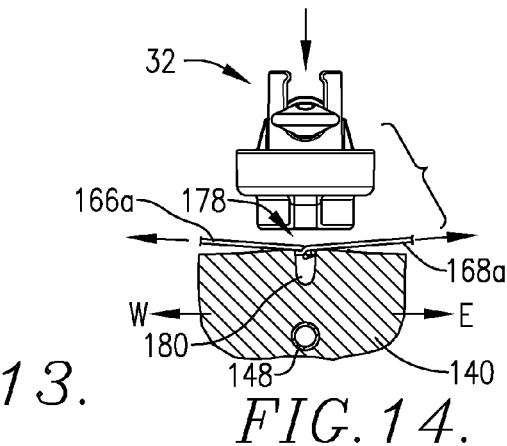
FIG. 14 is an end view in partial section illustrating the next step in the preferred method wherein the X-shaped stitch is tightened to invert the patient's skin adjacent the wound opening and the base of the apparatus is pressed downwardly over the stitch and wound opening.
Figure 15:
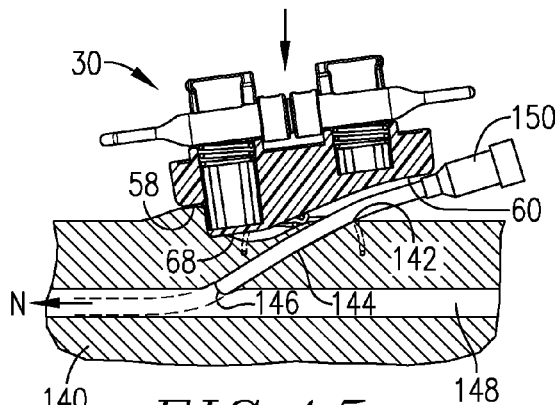
FIG. 15 is a sectional view of the steps depicted in FIG. 14.
Figure 16:
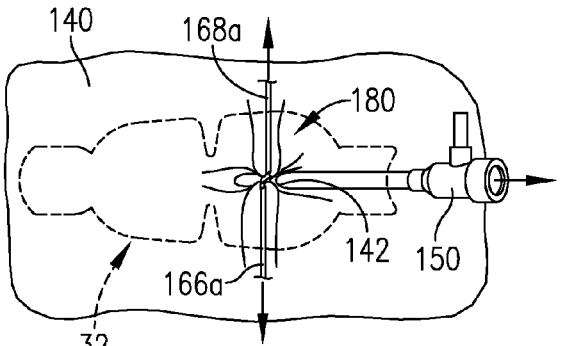
FIG. 16 is a top view of the steps illustrated in FIGS. 14 and 15, with the apparatus base illustrated in phantom and also showing withdrawal of the catheter sheath from the wound tract.
Figure 17:
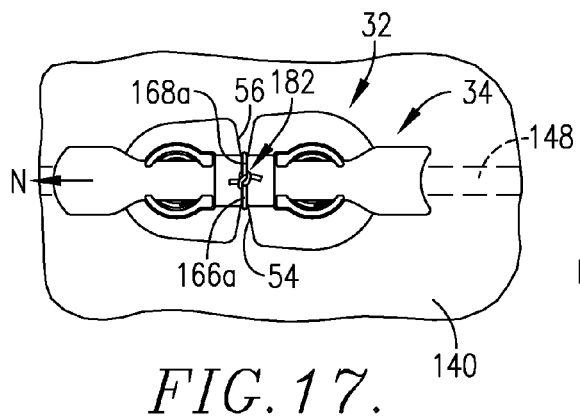
FIG. 17 is a top view of the next step of the method wherein the ends of the suture are passed around the rotatable operator forming a part of the apparatus base and knotted.
Figure 18:
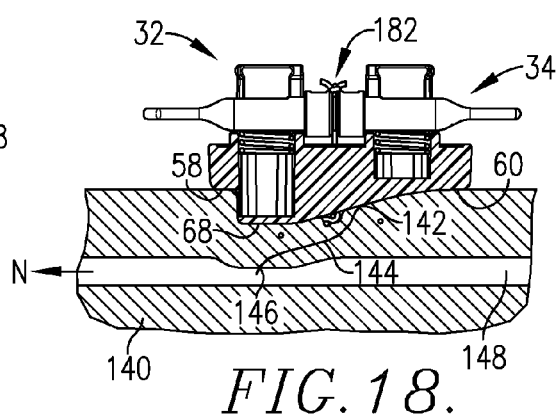
FIG. 18 is a sectional view illustrating the position of the apparatus base and operator after the tying and knotting step illustrated in FIG. 17.
Figure 19:
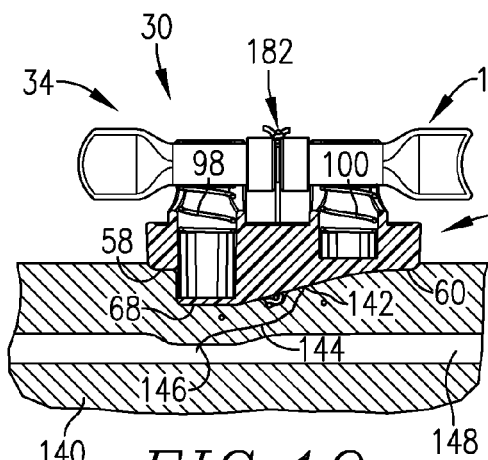
FIG. 19 is a view similar to that of FIG. 18, but illustrating the operator rotated to allow the force-exerting springs of the base to move from the cocked to the released position thereof so as to close the wound tract and reduce blood flow through the patient's artery adjacent the wound arteriotomy.
Figure 20:
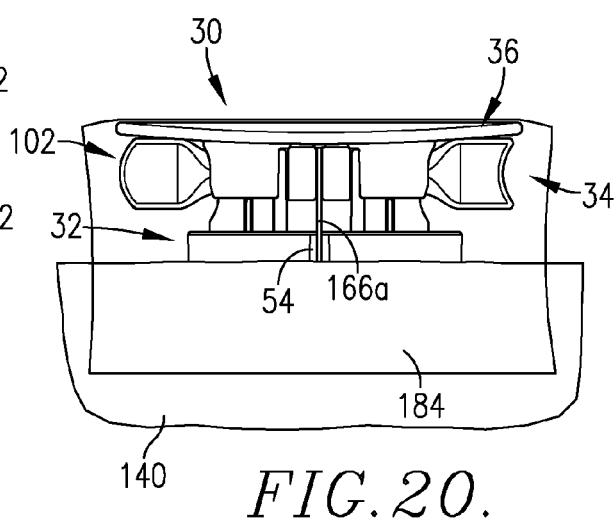
FIG. 20 is a side view of the installed apparatus with a cover secured to the base and with a stretch of adhesive passed over the cover and secured to the patient's tissue on opposite sides of the wound and apparatus.
Figure 21:
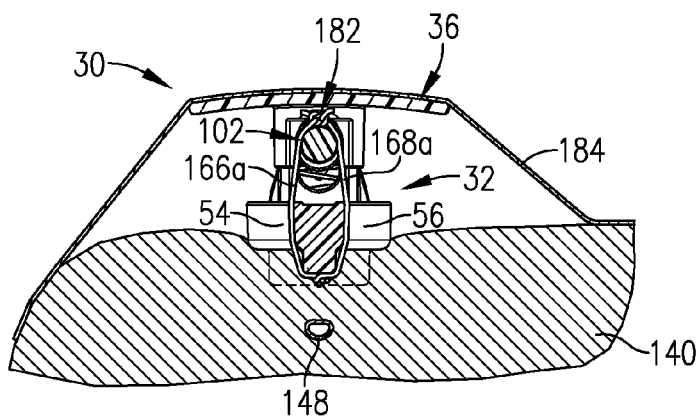
FIG. 21 is a vertical sectional view of the fully installed apparatus illustrated in FIG. 20.

The preferred method of using the apparatus 30 is depicted in FIGS. 11-23, in the context of the closure of a femoral artery puncture wound 138 (FIG. 12). It is to be understood, however, that the ensuing discussion is exemplary only, and that the invention can be used in virtually every type of endovascular arterial or venous intervention.

The wound 138 is in the groin tissue 140 of a patient and includes an insertion site 142, an elongated, obliquely extending tract 144 extending from insertion site 142 and terminating at an arteriotomy 146 in the femoral artery 148. A conventional catheter sheath 150 is positioned within the tract 144 in order to permit an endovascular procedure using a catheter (not shown). When the procedure is completed and the catheter removed, it is necessary to promptly close the wound 138 during removal of the sheath 150, while minimizing any blood loss and rendering the patient ambulatory in as short a period as possible.

In order to facilitate the description of the preferred wound closure technique, the direction towards the patient's heart is denominated as "north," whereas the direction leading away from the heart is denominated "south." Correspondingly, transverse directions are denominated as "east" and "west," respectively. Accordingly, it will be observed that the tract 144 extends from the insertion site 142 to the arteriotomy 146 in a generally northerly direction.

In the first step of the wound closure procedure, the endovascular physician creates a Z-stitch 154 (FIGS. 11-12) in the patient's tissue 140 by passing a suture 156 through an entrance 158 east of the artery 148 and south of insertion site 142, an exit 160 west of artery 148 and south of insertion site 142, an entrance 162 north of insertion site 142 and east of artery 148, and finally an exit 164. The end of the suture 156 adjacent entrance 158 is then clipped. The stitch 154 thus includes exterior suture stretches 166 and 168, embedded suture stretches 170 and 172 above artery 148 at a depth of less than about one-half inch, and an obliquely extending exterior stretch 174 extending between the exit 160 and entrance 162.

In the next step (FIG. 13), the exterior suture stretches 166 and 168 are crossed and interconnected by folding the stretches over each other, thereby creating an X-stitch 176 with a central suture fold 178, and with the free ends 166a, 168a of the exterior suture stretches 166, 168 extending westerly and easterly, respectively. Preferably, the suture fold 178 is positioned in very close proximity or over the insertion site 142.

The next step (FIGS. 14-18) requires two health care providers and generally involves tightening of the X-stitch 176 while the force-transmitting body 32 of apparatus 30 is positioned atop wound 138 with application of a downwardly directed force, and the sheath 150 is removed. In detail, one care provider grasps the free suture ends 166a, and 168a, and pulls these in an easterly and westerly direction, respectively. This serves to tighten the suture while inverting the patient's skin tissue, as illustrated by numeral 180, at the region of the insertion site 142. That is, uninvolved, parallel peripheral tissue is forced upwardly, while the central tissue adjacent the wound is pushed downwardly over the entire insertion site 142, tract 144, and arteriotomy 146. The inverted tissue in cross-section thus resembles an M in shape.

Once the skin is inverted, the second provider presses body 32 (which is in the spring-cocked position thereof) downwardly into the patient's tissue 140, while withdrawing the sheath 150. In particular, the body 32 is located in general north-south alignment with the artery 148, such that the force-transmitting surface sections 58 and 68 are above and north of insertion site 142 and arteriotomy 146, with the oblique section 64 over the suture fold 178, and with the rearmost portion of surface section 60 located south of the insertion site 142. As the body 32 is held in this position, the first provider, while still maintaining tension on the suture free ends 166a and 168a, pulls the ends upwardly through the body grooves 54 and over the central segment 104 of operator 102, and forms a secure knot 182 at the top surface of the segment 104. In this condition (see FIGS. 17-18) the artery upstream of arteriotomy 146 is partially closed, whereas tract 144 and arteriotomy 146 are fully closed.

In preferred practice, the suture ends 166a, 168a are pulled upwardly while avoiding any twisting prior to formation of the knot 182. This avoids reduction in the burst strength of the suture ends. That is, if the ends are twisted prior to knotting, the burst strength of the suture ends is reduced and can induce premature failure of apparatus 30.

In order to establish and maintain a substantially constant and time-invariant wound closure force, the operator 102 is rotated 90° so that the springs 98, 100 are released to their force-exerting positions (FIGS. 5-7 and 19). This serves to maintain the suture 156 in tension so as to firmly draw the body 32 into the wound-closure position while also maintaining a substantially even force based upon the strengths of the springs 98, 100. Preferably, the tensile force exerted on the suture 156 is slightly below the burst strength thereof; thus, the tensile force on suture 156 should typically be 10-15% less than the suture burst strength.

Next, the cover 36 is positioned atop body 32 by pressing the tubular members 126, 128 over the tubular member 74, 76 until the cover is firmly seated. At this point, a length of wide adhesive material 184 (e.g., 6×8 inches) is placed over the cover 36 with the ends of the material 184 being pulled downwardly and adhesively attached to the patient's tissue at east and west and north and south locations, respectively. This material 184 may be stretchable or non-stretchable, and if desired may be breathable. Placement of the material 184 serves to exert a secondary force through the body 32, in addition to that exerted by the springs 98, 100, while also stabilizing the apparatus 30 on the patient. Advantageously, the height of the apparatus 30 above insertion site 142 divided by the maximum east-west transverse dimension of the force-transmitting surface 72 is greater than 1. With this ratio, the vertical component of the force generated by the material 184 is increased, causing additional force to be applied over the entirety of the wound.

As finally positioned, the apparatus 30 creates targeted, asymmetric tissue pressures from north to south. At the north, a larger, non-occlusive pressure is applied upstream of the arteriotomy 146 in order to lower the patient's blood pressure and blood flow at the downstream arteriotomy. The transverse surface segment 68, positioned directly above the arteriotomy 146, closely mimics a properly executed two-handed manual wound closure. The lesser tissue pressures created south of the arteriotomy 146, owing to the decreasing force gradient generated through the oblique section 66, and the greater surface area of southernmost section 60, also are similar to such manual closure.

Figure 22:
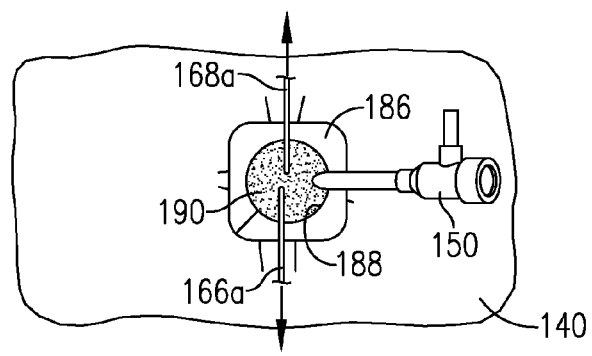
FIG. 22 is a top view of a preferred additional method step wherein a dam is placed around the wound opening and the sheath, and a hemostatic powder is deposited within the confines of the dam and over the wound opening.

FIG. 22 depicts another preferred aspect of the invention, namely the use of a compressible dam 186 having a central opening 188 over the wound. In particular, the dam is placed in surrounding relationship to the insertion site 142 and a hemostatic powder 190 is sprinkled into the opening 188 (about 0.3 g). This procedure is carried out prior to tensioning of the suture free ends 166a, 168a, and placement of the apparatus 30 on the wound site, as previously described. Of course, the dam remains in place during the entire closure sequence, and is then removed after closure. The hemostatic powder 190 may be a cationic surfactant combined with a strong acid cation exchange resin, or a potassium ferrate/strong acid cation exchange resin. Preferably, the powder 190 is of the type described in U.S. Pat. No. 6,187,347. In another embodiment, a sheet of exudate-absorbing woven or non-woven hemostatic material (such as oxidized cellulose or chitosan) may be used in lieu of or in addition to the powder 190.

Figure 23:
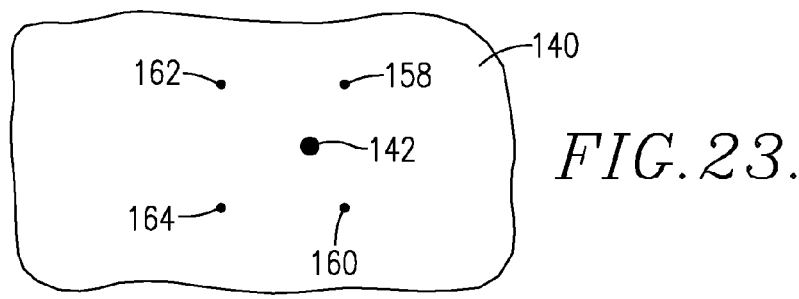
FIG. 23 is a top view of the condition of the patient's tissue after wound closure and with the patient ambulatory.

FIG. 23 illustrates the condition of the wound 138 at the completion of wound closure. After the appropriate closure time, the knotted suture 156 is cut and the apparatus 30 is removed from the wound 138. It will be seen that the insertion site 142 is closed (clotted) with the suture openings likewise closed. If desired or needed, a hemostatic/antiseptic powder can be sprinkled over the insertion site and the suture openings to help prevent infections and inhibit oozing. Normally, no dressing is required, and the loose powder is merely brushed off the wound site.

A significant advantage of the invention is that TTAs are substantially reduced. In the case of diagnostic procedures, TTAs on the order of 60 minutes are common, and with more complex interventional procedures, TTAs of 120 minutes are typical. In a pre-clinical study involving 100 patients with interventional procedures up to 12 Fr, the preferred apparatus of the invention closed the patients' wounds with no complications and TTAs of less than 120 minutes The invention also is useful with seriously obese patients. With such patients, the panniculus descends to the femoral insertion site, interfering with normal deployment of closure devices. This restricts the space around the wound and the ability of the healthcare professional to properly apply manual closure pressure. However, in the present invention, pre-compression of the springs 98, 100 and latching them with the operator 102 allows the device to be aligned over the wound and the knot 182 tied. Thereupon, the operator 102 is rotated to release the springs, and the material 184 is applied.

Those skilled in the art will appreciate that the preferred embodiment of the invention may be modified in many ways while still achieving the aims of the invention. For example, while identical springs 98, 100 are preferred, springs of different strengths and/or types may be used, e.g., flat and coiled springs. The springs may be attached to the lower body or the top cover of the apparatus, at the discretion of the designer. Additionally, the invention may be practiced without the use of the Z-stitch suture 156. In this embodiment, a spring force is generated directly against the top cover by manually placing the cover in direct contact with the spring(s). Then an adhesive material or film 184 is brought over the cover and pressed downwardly to compress the spring(s) and hold the device in place by adhering the film to the patient's skin on either side of the wound 138. Such an embodiment is useful, for example, on very thin elderly patients whose skin is so fragile that sutures are not effective to retain the device in place.

We claim:

1. A method of closing a wound in a patient's tissue, said wound presenting an insertion site opening and an elongated, obliquely oriented tract extending into said patient's tissue and in communication with said opening, said method comprising the steps of:

positioning a body in a wound-closing position proximal to the patient's skin and adjacent and in spanning relationship to said wound, said body having an elongated force-transmitting surface having a length greater than the width thereof and positioned in general axial alignment with said tract, at least a portion of said elongated force-transmitting surface being tapered along the length thereof; and exerting a force through said force-transmitting surface in order to close the wound, said force having different magnitudes of pressure at different locations along the length of said force-transmitting surface, said force being greatest adjacent one end of said force-transmitting surface closest to the patient's heart, and decreasing along the length of the force-transmitting surface away from the patient's heart.

2. The method of claim 1, including the step of exerting said force substantially invariantly over a period of time to close said wound.

3. The method of claim 1, said force-exerting step comprising the steps of passing a suture through the patient's tissue at a point adjacent to said insertion site, tying said body with the ends of said suture, and generating a mechanically-derived force in order to exert said force through said force-transmitting surface against the patient's tissue.

4. The method of claim 3, said body supporting a plurality of spaced apart springs and an operator engaging said springs, said operator shiftable between a first orientation maintaining said springs in a cocked position, and a second orientation allowing said springs to generate said mechanically-derived force, said force-exerting step comprising the step of shifting said operator to said second orientation, said operator comprising an elongated, axially rotatable paddle, said paddle having structure for maintaining said springs in said cocked position at a first orientation thereof, and for allowing the springs to exert said force upon rotation of the paddle to a second orientation.

5. The method of claim 4, said body having a pair of generally spaced apart tubular spring retainers with one of said plurality of springs within each retainer, said spring retainers each having recesses for receiving said operator and allowing selective axial rotation thereof, said operator having respective sections passing through said retainers and engaging the spring therein, said operator shiftable between a first spring-cocking position wherein said springs are held in said cocked positions thereof, and a second spring-releasing position wherein said springs are released from said cocked positions thereof.

6. The method of claim 5, said operator sections being generally oval in cross-section and presenting major and minor axes, said spring retainer recesses configured to retain said operator sections in said first positions thereof when the operator is oriented so that said major axes extend in one direction, and to release said springs when said operator is oriented with said major axes in a second, different direction.

7. The method of claim 1, said wound tract communicating with an opening formed in a vascular vessel within the patient's tissue, said body and force-exerting assembly cooperatively configured to reduce the blood pressure within and downstream of said vascular vessel.

8. A method of closing a wound in a patient's tissue, said wound presenting an insertion site opening and an elongated, obliquely oriented tract extending into said patient's tissue and in communication with said opening, said method comprising the steps of:

positioning a body in a wound-closing position proximal to the patient's skin and adjacent and in spanning relationship to said wound, said body having an elongated force-transmitting surface having a length greater than the width thereof and positioned in general axial alignment with said tract, at least a portion of said elongated force-transmitting surface being tapered along the length thereof; and exerting a force through said force-transmitting surface in order to close the wound, said force having different magnitudes of pressure at different locations along the length of said force-transmitting surface, said force-exerting step comprising the steps of passing a suture through the patient's tissue at a point adjacent to said insertion site, tying said body with the ends of said suture, and generating a mechanically-derived force in order to exert said force through said force-transmitting surface against the patient's tissue, said force-generating step comprising the step of exerting a force through a spring operably supported by said body.

9. The method of claim 8, said exerted force being greatest adjacent one end of said force-transmitting surface closest to the patient's heart, and decreasing along the length of the force-transmitting surface away from the patient's heart.

10. The method of claim 8, said body supporting a plurality of spaced apart springs and an operator engaging said springs, said operator shiftable between a first orientation maintaining said springs in a cocked position, and a second orientation allowing said springs to generate said mechanically-derived force, said force-exerting step comprising the step of shifting said operator to said second orientation, said operator comprising an elongated, axially rotatable paddle, said paddle having structure for maintaining said springs in said cocked position at a first orientation thereof, and for allowing the springs to exert said force upon rotation of the paddle to a second orientation.

* * * * *